United States Patent [19]

Kirk et al.

[11] Patent Number: 5,375,592
[45] Date of Patent: Dec. 27, 1994

[54] CARBON DIOXIDE DETECTOR AND SHIELD

[76] Inventors: Gilbert M. Kirk, 2222 Arbor Crest Dr., Carrollton, Tex. 75007; James D. Bickley, 2403 Old Mill Rd., Dallas, Tex. 75287

[21] Appl. No.: 45,518

[22] Filed: Apr. 8, 1993

[51] Int. Cl.$^5$ ............... A61M 16/00; A61B 5/08; G01N 30/00
[52] U.S. Cl. .......... 128/207.14; 128/200.26; 128/719; 116/206; 116/DIG. 41; 73/23.3; 422/85; 422/87; 436/900
[58] Field of Search .............. 116/206, DIG. 41; 128/716, 719, 202.22, 205.25, 200.24, 200.26, 207.14, 205.27; 73/23.3, 31.05; 422/83-89, 55-59; 436/133, 145, 900

[56] References Cited

U.S. PATENT DOCUMENTS

| | | | |
|---|---|---|---|
| 3,373,735 | 3/1968 | Gallagher | 116/206 X |
| 3,556,122 | 1/1971 | Laerdal | 137/102 |
| 3,612,048 | 10/1971 | Takaoka et al. | 128/188 |
| 3,615,233 | 10/1971 | Doering et al. | 23/252 |
| 3,752,654 | 8/1973 | Johannisson | 128/205.28 X |
| 4,077,404 | 3/1978 | Elam | 128/145.8 |
| 4,365,627 | 12/1982 | Wing | 116/206 X |
| 4,440,162 | 4/1984 | Sewell et al. | 128/202.22 |
| 4,728,499 | 3/1988 | Fehder | 422/56 |
| 4,774,941 | 10/1988 | Cook | 128/205.13 |
| 4,790,327 | 12/1988 | Despotis | 128/719 |
| 4,879,999 | 11/1989 | Leiman et al. | 128/207.14 |
| 4,928,687 | 5/1990 | Lampotang et al. | 128/207.14 |
| 4,945,918 | 8/1990 | Abernathy | 128/719 |
| 4,994,117 | 2/1991 | Fehder | 436/133 |
| 5,005,572 | 4/1991 | Raemer et al. | 128/207.14 |
| 5,109,840 | 5/1992 | Daleiden | 128/205.13 |
| 5,124,129 | 1/1992 | Riccitelli et al. | 422/56 |
| 5,166,075 | 11/1992 | Fehder | 436/133 |
| 5,179,002 | 1/1993 | Fehder | 435/25 |

FOREIGN PATENT DOCUMENTS

| | | |
|---|---|---|
| 0139363 | 5/1985 | European Pat. Off. |
| 3818783 | 12/1989 | Germany |
| 2139099 | 11/1984 | United Kingdom |
| 2218515 | 11/1989 | United Kingdom |
| 8907956 | 9/1989 | WIPO |
| 8907957 | 9/1989 | WIPO |

OTHER PUBLICATIONS

Robert Weast, ed., *CRC Handbook of Chemistry & Physics*, 64th ed. (Boca Raton, Fla.: CRC Press, 1983) pp. D-152-3.

*Primary Examiner*—Edgar S. Burr
*Assistant Examiner*—Eric P. Raciti
*Attorney, Agent, or Firm*—Baker & Botts

[57] ABSTRACT

An apparatus (14) for detecting carbon dioxide in exhaled gas is disclosed. The apparatus comprises an indicating element (10) for changing color when exposed to carbon dioxide and a carbon dioxide shield (12) for absorbing a predetermined level of carbon dioxide from the exhaled gas before exposing the indicating element (10) to the exhaled gas.

10 Claims, 2 Drawing Sheets

CARBON DIOXIDE DETECTOR AND SHIELD

TECHNICAL FIELD OF THE INVENTION

The invention relates generally to the field of medical devices, Specifically, the invention relates to a carbon dioxide detector and shield and more particularly to a carbon dioxide detector and shield for detecting the presence of carbon dioxide in a patient's respiratory gas,

BACKGROUND OF THE INVENTION

In hospitals, as well as emergency medical situations, it is a common practice when a patient is having difficulty breathing or not breathing at all to apply resuscitation to assist breathing. One approach is to use an endotracheal tube inserted in the patient's trachea to facilitate the passage of air into and out of the lungs to maintain proper respiration. Another approach is to use a bag-mask-valve system. Trained hospital clinicians and emergency medical specialists are concerned that the endotracheal tube is properly placed into the trachea and not into the esophagus. In the bag-mask-valve system, the medical professional's concern is proper cardio-pulmonary function. The patient's breathing must then be monitored over a relatively long period of time in order to ensure continuous respiration, Increasing concern for the proper placement of the endotracheal tube has alerted medical practitioners to seek every aid possible to ascertain the correct location of the endotracheal tube for short term and long term detection and monitoring.

Quantitative electronic analyzers provide an accurate reading of carbon dioxide levels but they are expensive, requiring minutes of warm-up time, frequent calibration and are not suitable for field use.

Fiberoptic laryngoscopes are also a method for determining accurate placement of the endotracheal tube but are very expensive, requiring specialized training. This method allows for determining correct placement but is of no value for long term patient monitoring.

Devices for the detection of carbon dioxide which use chemical compounds that change color when exposed to carbon dioxide are known in the art for determining and detecting the correct placement of an endotracheal tube into the trachea.

U.S. Pat. No. 4,691,701 discloses a method for detecting the correct placement of an endotracheal tube following intubation of a patient. The indicator is in the form of a transparent disc which sealingly engages an aperture in the housing. The disc has a chemical substance which produces a color change indication when exposed to carbon dioxide from a patient. Although this patent provides for a chemical substance applied to a litmus type paper, it requires a disk for connecting to the device and allows for a one time color change which occurs only for a very brief period.

U.S. Pat. No. 4,728,499 discloses a device for detecting carbon dioxide in a gas which comprises a housing having an inlet and an outlet with a clear visualization window for viewing the change of color of the chemically treated strip.

U.S. Pat. No. 4,994,117 discloses a device for detecting carbon dioxide in a gas which comprises a housing having an inlet and an outlet with a clear visualization window for viewing a chemically treated strip that provides various colors indicating the carbon dioxide concentration.

U.S. Pat. No. 5,166,075 discloses a method for determining the presence of carbon dioxide in a sample of respiratory gas in concentration of at least 2% within a diagnostically effective period of time (two to ten seconds) while an indication of the presence of carbon dioxide in a sample of ambient air (0.03% carbon dioxide) would be delayed beyond a predetermined period of time (ten minutes).

The various devices and compositions disclosed in the above mentioned patents provide means for detecting or indicating the presence of carbon dioxide under certain circumstances. However, none of the devices address the problem of a false positive indication of carbon dioxide. During intubation, residual levels of 0.5% to 1.5% of carbon dioxide may be in the airway and the esophagus and stomach which may indicate a color change to the practitioner and give the false sign that the tube is correctly placed in the trachea.

Also, none of the aforementioned patents discuss or address the problem of the ambient air sensitivity such indicators have when exposed to ambient air prior to use. Very careful attention must be placed to opening or exposing the device to ambient air immediately prior to use. This is very difficult due to the unpredictability of the timing of the procedure as to when to expose the device to ambient air prior to use, plus the fact that the practitioner is extremely preoccupied with the patient and would find any distraction not allowing as much pre-setup as possible as a severe disadvantage of the device.

Also the various prior devices address only determining the correct placement of an endotracheal tube and do not directly discuss the problems associated with monitoring the patient for a long period of time, either continuously or intermittently. It is known that the concentration of carbon dioxide in the atmosphere is about 0.03% and the concentration of carbon dioxide in the exhaled breath of a person is normally 4.0% to 5.0%.

However, none of the devices used to determine proper placement of an endotracheal tube in a trachea addresses the problem of false positive indication of carbon dioxide. Such false positive indication can occur when the endotracheal tube for example, is erroneously placed in the esophagus and the stomach contains residual levels of carbon dioxide high enough to cause a change in color on the carbon dioxide indicator. This will erroneously indicate that the endotracheal tube has been placed in the trachea.

One other problem with the foregoing devices is that they show a gradual color change which is proportional to the amount of carbon dioxide in the sample of gas being tested. Such gradual change of color makes it difficult to determine when the level of respiration of a person is sufficient. Additionally, none of the devices that are available exhibit insensitivity to exposure to ambient air before use. Such exposure to ambient air could cause a color change which may falsely indicate correct placement of an endotracheal tube in the trachea and proper respiration.

Another problem with prior devices is that they do not provide for low dead space. For instance, the maximum allowable dead space for a resuscitator per ASTM is 30 ml for adults, 15 ml for children and 7 ml for infants. One of the problems with known devices is that they add unacceptable levels of dead space. One of the known devices adds over 30 ml of dead space.

SUMMARY OF THE INVENTION

Therefore, a need has arisen for a device which will indicate the proper placement of an endotracheal tube, function to continuously monitor the respiration of a person and indicate whether or not such respiration is sufficient, exhibit insensitivity to ambient air contamination prior to its use and provide for low dead space.

The present invention provides a device to aid practitioners to quickly ascertain the correct location of an endotracheal tube following intubation. The present invention also will allow the determination of the placement of the endotracheal tube, continuous monitoring of a patient's carbon dioxide, avoid false positive indication and provide a colorimetric sensor which provides extended exposure to ambient air allowing set-up prior to use all with the addition of very little dead space (approximately less than 2 ml).

This invention provides a method and apparatus for detecting and monitoring the presence of less than approximately 2.2% carbon dioxide after approximately one minute and carbon dioxide levels of 3.5% or higher within a diagnostically effective period of time (two to ten seconds). Ambient air levels of exposure of 0.03% carbon dioxide will not show a color change for an extended period of time (up to eight hours or longer).

In another aspect of the present invention, an apparatus for detecting carbon dioxide in exhaled air is provided. The device comprises a housing defined by walls and having a transparent window in one of the walls, an inlet and an outlet. The housing has mounted therein an indicating element positioned to be viewed through the transparent window. The housing has a shield adjacent to the indicating element wherein the shield is chemically treated to protect the indicating element from low levels of carbon dioxide and ensure less sensitivity to prolonged ambient air exposure.

A technical advantage of the present invention is that a carbon dioxide indicator is provided that is insensitive to exposure to the atmosphere. Another technical advantage is that a carbon dioxide detector is incorporated into a breathing circuit with minimal increases to the dead space.

BRIEF DESCRIPTION OF THE DRAWINGS

Other aspects of the invention and their advantages will be discerned with reference to the following detailed description in conjunction with the appended drawings, in which.

DETAILED DESCRIPTION OF THE INVENTION

Figure 1:
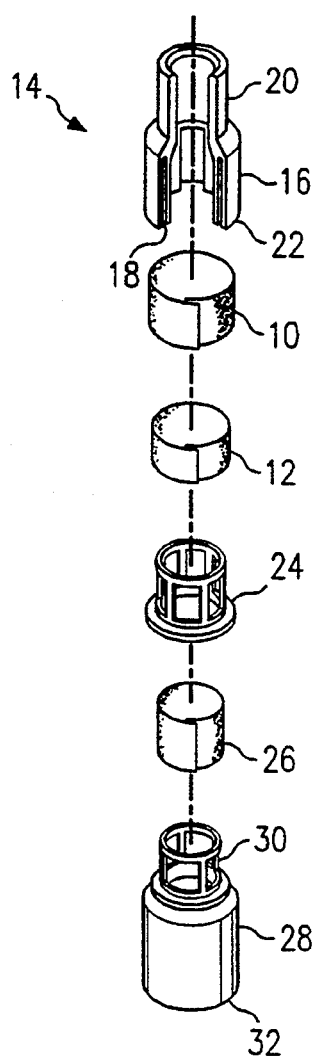
FIG. 1 is an adapter assembly incorporating the carbon dioxide indicator and shield in accordance with the present invention.

Referring to FIG. 1 a carbon dioxide indicator 10 and a carbon dioxide shield 12 are shown as part of adapter housing assembly 14. When assembled, any sample of air which is exposed to indicator 10 must first pass through shield 12. Carbon dioxide shield 12 is treated to absorb carbon dioxide in such a way that for concentrations of carbon dioxide which are found in a trachea, the color of indicator 10 will change within a clinically significant period of time (less than ten seconds). Normal levels of carbon dioxide are approximately 4.0% to 5.0%. Additionally, exposure to the shield 12 and indicator 10 combination to ambient air which normally has carbon dioxide levels of approximately 0.03%, will not cause a change in color of indicator 10 for eight hours or longer. Additionally, another advantage of the carbon dioxide shield 12 is to cause the color of indicator 10 to change color rapidly avoiding intermediary colors, making it much more apparent when proper endotracheal tube placement is achieved and respiration is normal. The shield 12 absorbs carbon dioxide at a predetermined rate which we refer to as it's threshold limit. This threshold, when exceeded by a normal respiratory gas allows exposure to the indicator 10, therein exhibiting a rapid color change. The shield will not allow low levels of carbon dioxide to effect the indicator. However, when the level of carbon dioxide in the air sample exposed to shield 12 reaches approximately 3.5% or higher, shield 12 cannot absorb the carbon dioxide as rapidly as the carbon dioxide is being supplied and the shield 12 allows the exposure of carbon dioxide to the indicating element. Finally, when exposed to carbon dioxide levels of approximately 0.03% (the level of carbon dioxide normally found in ambient air), the threshold of the shield 12 will not be exceeded protecting the indicator. In this way, the shield 12 indicator 10 combination will indicate proper placement of an endotracheal tube in a trachea within a clinically significant time.

By selecting shield 12 with a predetermined threshold level, different concentrations of carbon dioxide exposure can be displayed. This invention is made in such a way so that no color change occurs within a predetermined period of time when exposed to ambient air having a concentration of approximately 0.03% carbon dioxide. In one embodiment, such predetermined period of time is approximately eight hours. Additionally, the current invention is formed so that in an air sample containing a level of carbon dioxide of approximately 2.5% that no color change occurs within a second predetermined time. In one embodiment such second predetermined period of time is approximately 60 seconds. Further, such current invention is made so that a color change occurs during a third period of time when the indicator or indicating element 10 is exposed to an air sample containing approximately 3.5% carbon dioxide. In one embodiment, such period of time is approximately 2 to 10 seconds.

The chemical formula for the indicating element 10 is comprised of the following ingredients. Mix together 300 cc de-ionized water, 0.072 grams calcium hydroxide ($Ca[OH]_2$), and 0.06 grams sodium hydroxide (NaOH). Purge with nitrogen ($N_2$) until dissolved. Check with Ph meter which should read approximately 12.0.

Add 0.1 gram creosol red sodium salt, 0.02 grams M-creosol purple sodium salt, 100 cc propylene glycol ($C_3H_8O_2$), and 20 cc glycerol ($C_3H_8O_3$). Purge with nitrogen ($N_2$). Imbibe Whatman No. 1 filter paper or equivalent. Dry under hot air stream.

Many of the above ingredients can be prepared in advance in stock solutions for ease of manufacturing. After indicator 10 is made, it must be protected and sealed from the ambient air during its shipping and storage.

The carbon dioxide shield 12 is created by applying a $CO_2$ absorbing substance onto a carrier, into a bag or pouch, or between filters and placing it in contact with the exhaled gas. In the preferred embodiment, the shield 12 is in contact alternatively with exhaled and inhaled gases. Bases are generally suitable for absorbing $CO_2$ and the following compounds are examples of some of the suitable bases: sodium hydroxide, calcium hydroxide, magnesium hydroxide, lithium hydroxide, potassium hydroxide, sodium carbonate, and potassium carbonate. The base can be used in powder or crystal form with a protecting means to prevent exposing the patient to the said chemicals. In an alternative method, the shield 12 is created by bubbling the exhaled gas through a liquid base solution before exposing the indicator 10 to the gas.

In the preferred embodiment, the carbon dioxide shield 12 is made in the following way. First, a solution is made by dissolving sodium hydroxide in water. The relationship between sodium hydroxide and water is approximately 1 gram of sodium hydroxide for every 10 milliliters of water. This range of concentration can be varied to effect the threshold. Absorbent material is dipped into the sodium hydroxide solution. In one embodiment the material is Whatman No. 1 filter paper. The dipped material is then dried under a hot air stream for approximately one minute. In one method the temperature of the hot air stream is approximately 150°. The carbon dioxide shield 12 is then stored in a carbon dioxide free environment.

Still referring to FIG. 1 carbon dioxide indicator 10 is shown formed into a hollow cylindrical shape having a first diameter. Carbon dioxide shield 12 is also formed into a similar cylindrical shape which is hollow and has a second diameter which is slightly less than first diameter so that the shield can fit inside the indicator 10. A patient connection housing 16 is shown having a cylindrical slot 18 formed inside. The diameter of the cylindrical slot 18 is approximately equal to the first diameter so that indicator 10 can fit inside cylindrical slot 18. Patient connection housing 16 also includes a patient connecting port 20 which has a 22 mm outer diameter and a 15 mm inner diameter for connecting to endotracheal tubes, face masks, etc. After indicator 10 is inserted into slot 18, shield 12 is inserted into the main portion 22 of patient housing 16. An outer retainer 24 having slotted walls is provided. The diameter of this outer retainer 24 being slightly less than the second diameter. The outer retainer 24 is inserted into the main portion of patient connection housing 16 and acts to retain the shield 12 in its proper position. A barrier filter 26 which is in a cylindrical shape and has a diameter slightly less than the inner diameter of the outer retainer 24, is inserted through the middle of outer retainer 24. Filter 26 acts to filter out any products accompanying the respiratory gases such as salvia, etc. A retaining housing 28 with an inner retainer 30 is provided, inner retainer 30 having a diameter slightly less than that of barrier filter 26 and insertable in through barrier filter 26 to retain it in place. The retaining housing 28 is then sealingly coupled to patient connection housing 16. Retaining housing 28 also has an oxygen supply port 32. The end result is that retainer housing assembly 14 creates an air tight chamber into which gases may flow only through either the patient connecting port 20 or oxygen supply port 32.

Figure 2:
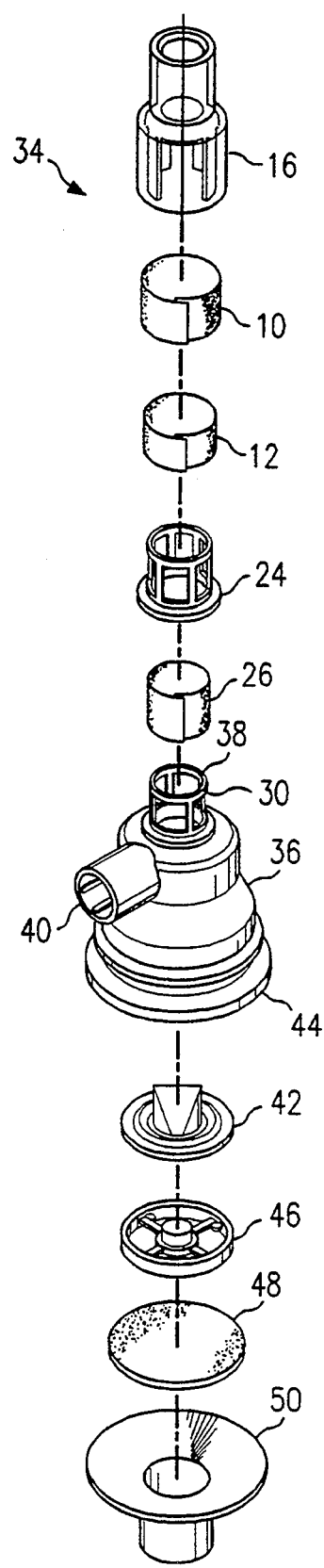
FIG. 2 is a regulator with filter and port for connecting to breathing apparatus incorporating the carbon dioxide indicator and shield in accordance with the present invention.

Referring to FIG. 2 a regulator assembly 34 is shown. Regulator assembly 34 substantially incorporates the retainer housing assembly 14 of FIG. 1. The only difference is that inner retainer 30 is now part of patient valve housing 36 which has an inhale port 38 and an exhale port 40. A duckbill valve 42 is inserted into oxygen supply port 44 of patient valve housing 36. A duckbill retainer 46 is inserted into oxygen supply port 44 in order to retain duckbill valve 42 in place. Duckbill valve 42 acts in such a way to allow airflow out of patient valve housing 36, such an airflow that is created when a patient inhales through patient connecting port 20 of patient connection housing 16. When a patient exhales, thus creating an airflow into patient valve housing 36 via inhale port 38, duckbill valve acts to direct the airflow out of exhale port 40. In this way during inhalation oxygen is supplied through oxygen supply port or inlet opening 44 and the exhaled respiratory gases are directed through exhale port 40 so as not to contaminate the oxygen supply. A bacterial filter 48 is supplied to filter the oxygen being fed into oxygen supply port 44. A gas inlet adapter 50 is supplied to facilitate connection to a supply of oxygen.

Figure 3:
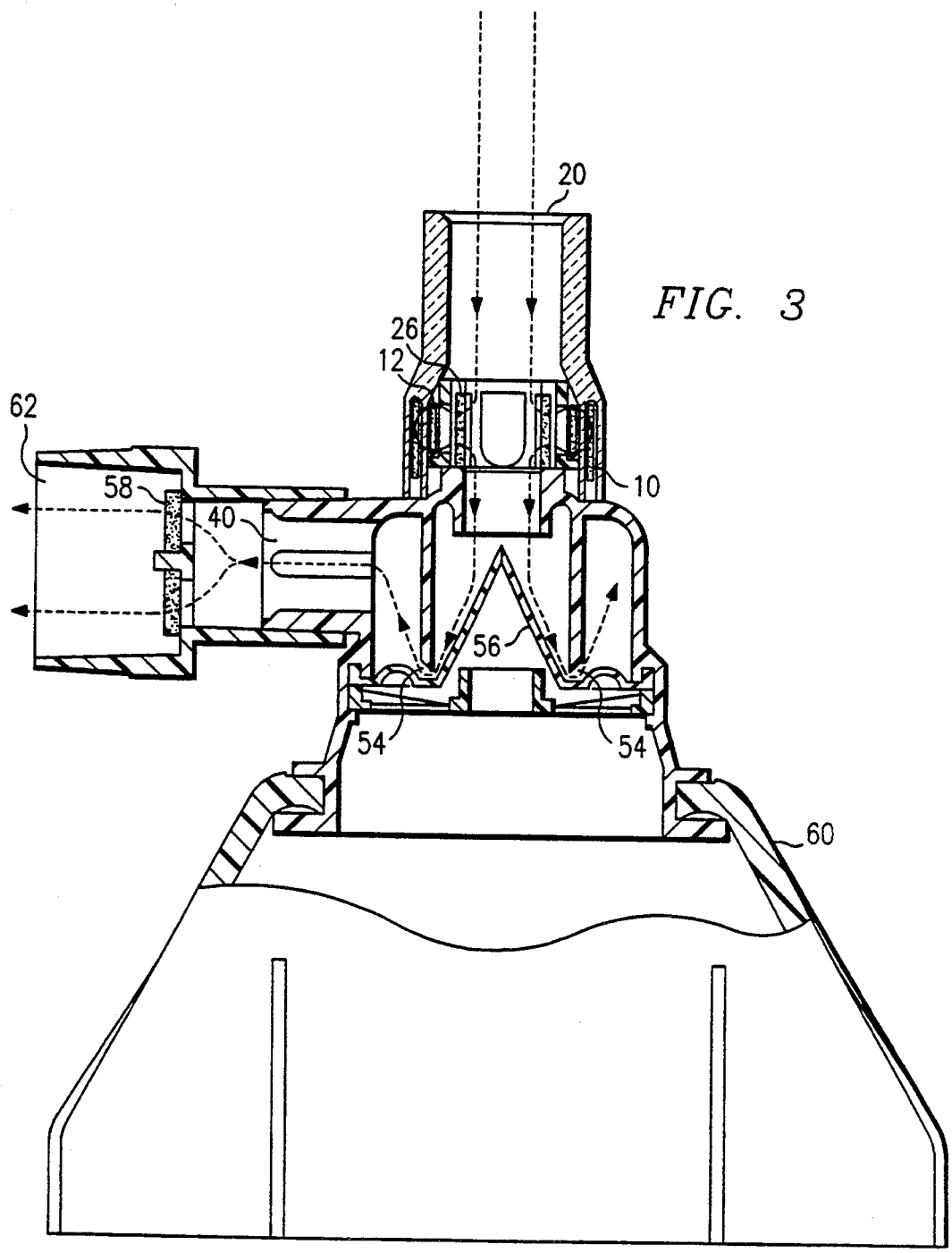
FIG. 3 is a cut away view of the regulator of FIG. 2.

The air flow which is set up within patient valve housing 36 due to the action of duckbill valve 42 can be more fully understood by referring to the air flow directions shown in FIG. 3. Referring to FIG. 3, the operation of regulator assembly of FIG. 2 is more fully shown. As a patient exhales, exhaled gas is forced into patient connecting port 20 through barrier filter 26 carbon dioxide shield 12 and indicating element 10, out through openings 54 created by the closing of duckbill valve flaps 56. The exhaled gas continues on out through exhale port 40 and optional exhalation port assembly 62. Exhale port 62 includes a flap valve 58 which prevents air from entering into patient valve housing 36 from exhale port 40.

When the patient inhales, duckbill valve flaps open and flap valve 58 closes thus creating an air flow into the patient's lungs which starts from oxygen supply 60 and flows through the center of duckbill valve 42 and right up through inner retainer 30. Thus, on inhalation, the inhaled oxygen bypasses barrier filter 26, carbon dioxide shield 12 and carbon dioxide indicating element 10 and goes directly into the patient's lungs. However, indicating element 10 is exposed to enough oxygen so that it is purged.

The preferred responsive indication is such that no color change occurs for twenty-five minutes or greater up to the shelf life of the device in the presence of ambient air but a color change is produced preferably within one to fifteen seconds in the a gaseous sample of at least about 3.5% carbon dioxide, and producing no color change of a gaseous sample of at about 2.2% carbon dioxide for a period of at least sixty seconds.

The preferred embodiment provides a device to detect and monitor the presence of carbon dioxide during resuscitation with a face mask or endotracheal tube at a level high enough to prevent false positive indication of endotracheal tube placement during patient ventilation. The preferred embodiment provides a device which prior to actual usage can be set-up in ambient air (0.03% carbon dioxide) with the necessary fixtures or accessories attached for preset-up requirements allowing accessibility of the device to the practitioner under current standard operation procedures, not requiring opening immediate prior to use as in all other said devices.

While the invention has been particularly shown and described in the foregoing Detailed Description, it will be understood by those skilled in the art that various other changes in form and detail may be made without departing from the spirit and scope of the invention.

What is claimed is:

1. Apparatus for detecting carbon dioxide in exhaled gas comprising:
   an indicating means for changing color in the presence of carbon dioxide;
   a carbon dioxide shield, associated with the indicating means, for absorbing up to a predetermined threshold concentration of carbon dioxide; and
   a housing for receiving the exhaled gas and for displaying the indicating element.

2. The apparatus of claim 1 having first and second openings for serially connecting to a respiratory supply line.

3. The apparatus of claim 1 wherein said carbon dioxide shield comprises either sodium hydroxide or calcium hydroxide.

4. The apparatus of claim 1 wherein said housing is constructed out of a clear material.

5. The apparatus of claim 1 wherein said indicating element and said carbon dioxide shield occupy a low dead space.

6. The apparatus of claim 1 wherein said predetermined threshold concentration of carbon dioxide is at least about 2.2%.

7. The apparatus of claim 1 wherein said indicating means and said carbon dioxide shield are contained in a dead space of less than 50 cc.

8. Apparatus of claim 1 wherein said $CO_2$ shield comprises a strip carrier.

9. Apparatus of claim 1 wherein said indicating means, after indicating the presence of $CO_2$, changes color indicating the absence of $CO_2$.

10. A method for detecting carbon dioxide in gas exhaled by a patient comprising the steps of:
    shielding a carbon dioxide detector from the flow of exhaled gas with a carbon dioxide absorption element on a strip carrier;
    absorbing the carbon dioxide below predetermined threshold concentration;
    exposing the carbon dioxide detector to exhaled gas having the predetermined amount of carbon dioxide removed to effect a color change in the detector; and
    displaying the changed color of said carbon dioxide detector indicating the concentration of carbon dioxide in the exhaled gas.

* * * * *